(12) United States Patent
Apetri et al.

(10) Patent No.: US 11,274,147 B2
(45) Date of Patent: Mar. 15, 2022

(54) BINDING MOLECULES THAT SPECIFICALLY BIND TO TAU

(71) Applicant: JANSSEN VACCINES & PREVENTION B.V., Leiden (NL)

(72) Inventors: Constantin Adrian Apetri, Noordwijkerhout (NL); Jaroslaw Juraszek, Amsterdam (NL); Roosmarijn Janson, Leiden (NL); Harmke Cornelia Verveen, Leiden (NL); Bunga Berdien Siregar, Amstelveen (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 0 days.

(21) Appl. No.: 16/965,565

(22) PCT Filed: Jan. 31, 2019

(86) PCT No.: PCT/EP2019/052324
§ 371 (c)(1),
(2) Date: Jul. 28, 2020

(87) PCT Pub. No.: WO2019/149798
PCT Pub. Date: Aug. 8, 2019

(65) Prior Publication Data
US 2021/0047393 A1 Feb. 18, 2021

(30) Foreign Application Priority Data
Feb. 1, 2018 (EP) .................... 18154685

(51) Int. Cl.
*C07K 16/18* (2006.01)
*C07K 14/47* (2006.01)
*A61P 25/28* (2006.01)
*A61P 25/16* (2006.01)

(52) U.S. Cl.
CPC .......... *C07K 16/18* (2013.01); *C07K 2317/21* (2013.01); *C07K 2317/34* (2013.01); *C07K 2317/565* (2013.01); *C07K 2317/76* (2013.01)

(58) Field of Classification Search
None
See application file for complete search history.

(56) References Cited

FOREIGN PATENT DOCUMENTS

| WO | 00/63403 A2 | 10/2000 |
|---|---|---|
| WO | 2010/142423 A2 | 12/2010 |
| WO | 2014/016737 A1 | 1/2014 |
| WO | 2015/197823 A3 | 12/2015 |

(Continued)

OTHER PUBLICATIONS

Rafii, Michael S. et al., "Recent developments in Alzheimer's disease therapeutics," BMC Medicine, vol. 7(7), doi: 103.1186/1741-7015-7-7, 4 pages, 2009 (Year: 2009).*

(Continued)

*Primary Examiner* — Aurora M Fontainhas
(74) *Attorney, Agent, or Firm* — Kramer & Amado, P.C.

(57) ABSTRACT

The invention relates to binding molecules and antigen-binding fragments that specifically bind to microtubule-associated protein tau. The invention also relates to diagnostic, prophylactic and therapeutic methods using the binding molecules or antigen-binding fragments.

19 Claims, 2 Drawing Sheets

Specification includes a Sequence Listing.

○ hCBTAU-22.1
▼ hCBTAU-22.1 (S52R[VH])
△ hCBTAU-22.1 (N33F[VH];S52R[VH])
● hCBTAU-22.1 (S30R[VH];N33F[VH];S52R[VH])
◇ hCBTAU-22.1 (S30R[VH];N33F[VH];P52$_A$R[VH])
■ hCBTAU-22.1 (N33F[VH];S52R[VH];Q27R[VL])
□ hCBTAU-22.1 (N33F[VH];P52$_A$R[VH];Q27R[VL])

(56) References Cited

FOREIGN PATENT DOCUMENTS

WO 2017/009308 A3 7/2016

OTHER PUBLICATIONS

Abhinandan, et al., "Analysis and improvements to Kabat and structurally correct numbering of antibody variable domains", Molecular Immunology, 45, 3832-3839 (2008).

Almagro, "Identification of differences in the specificity-determining residues of antibodies that recognize antigens of different size: implications for the rational design of antibody repertoires", Journal of Molecular Recognition J. Mol. Recognit., 17, pp. 132-143 (2004).

Barghorn, et al., "Purification of Recombinant Tau Protein and Preparation of Alzheimer-Paired Helical Filaments in Vitro", Methods in Molecular Biology, vol. 299: Amyloid Proteins: Methods and Protocols, pp. 35-51. (downloaded Jul. 24, 2020), 2005.

Boutajangout, et al., "Passive immunization targeting pathological phospho-tau protein in a mouse model reduces functional decline and clears tau aggregates from the brain", Journal of Neurochemistry, vol. 118, pp. 658-667. (2011).

Chai, et al., "Passive Immunization with Anti-Tau Antibodies in Two Transgenic Models: Reduction of Tau Pathology and Delay of Disease Progression", The Journal of Biological Chemistry vol. 286, No. 39, pp. 34457-34467. (Sep. 30, 2011).

Chothia, et al., "Canonical Structures for the Hypervariable Regions of Immunoglobulins", J. Mol. Biol., 196, pp. 901-917. (1987).

Cragg, "CD20 antibodies: doing the time warp", Blood, vol. 118, No. 2, pp. 219-221. (Jul. 14, 2011).

Gendron, et al., "The role of tau in neurodegeneration", Molecular Neurodegeneration, 4:13, 19 pages. (2009).

Holmes, et al., "Proteopathic tau seeding predicts tauopathy in vivo", PNAS, 111, pp. E4376-E4385. (Jun. 20, 2014).

Khlistunova, "Inducible Expression of Tau Repeat Domain in Cell Models of Tauopathy: Aggregation is Toxic to Cells but Can Be Reversed by Inhibitor Drugs", The Journal of Biological Chemistry, vol. 281, No. 2, pp. 1205-1214. (Jan. 13, 2006).

Morris, M., et al. "The Many Faces of Tau", Neuron 70, pp. 410-426. (2011).

Lefranc, Marie-Paul, et al. "IMGT unique numbering for immunoglobulin and T cell receptor variable domains and Ig superfamily V-like domains", Development & Comparative Immunology, 27, pp. 55-77. (2003).

Wu, T. T., "An Analysis of the Sequences of the Variable Regions of Bence Jones Proteins and Myeloma Light Chains and Their Implications for Antibody Complementarity", J Exp Med 132, pp. 211-250. (1970).

Hanger, D. P. "Tau phosphorylation: the therapeutic challenge for neurodegenerative disease", Trends Mol Med, 15, pp. 112-119. (2009).

\* cited by examiner

BINDING MOLECULES THAT SPECIFICALLY BIND TO TAU

Pursuant to 37 C.F.R. § 1.821(c) or (e), this application contains a sequence listing, which is contained on an ASCII text file entitled "Sequence Listing" (SYT 3062 0311 WO 00 ORD sequence listing_ST25.txt, created Jul. 7, 2020, having a size of 15,756 bytes), which is herein incorporated by reference.

FIELD OF THE INVENTION

The invention relates to medicine. The invention in particular relates to binding molecules, e.g. antibodies or antigen-binding fragments thereof, that specifically bind to tau, and that are capable inhibiting the spreading of tau seeds. The invention also relates to diagnostic, prophylactic and therapeutic methods using the anti-tau binding molecules.

BACKGROUND OF THE INVENTION

Dementia is a syndrome that can be caused by a number of progressive disorders that affect memory, thinking, behavior and the ability to perform everyday activities. About 36 million people worldwide are suffering from dementia today. The number of people with dementia is projected to double by 2030, and more than triple to 115.4 million people by 2050. Alzheimer's disease (AD) is the most common type of dementia. Currently, one in nine people age 65 and older (11 percent) and nearly half of those over age 85 have Alzheimer's disease. According to Alzheimer's Disease International, current global costs of caring for these patients exceeds $600 billion annually. These costs are likely to rise even faster than the prevalence of disease, especially in the developing world, as more formal social care systems emerge, and rising incomes lead to higher opportunity costs.

The brains of AD patients have an abundance of two abnormal structures, the amyloid plaques and intracellular neurofibrillary tangles (NFTs). This is especially true in certain regions of the brain that are important in memory. There is also a substantial loss of neurons and synapses in the cerebral cortex and certain subcortical regions. Both neurofibrillary tangles and neuronal loss increase in parallel with the duration and severity of illness and neurofibrillary load has been shown to correlate with cognitive decline.

The neurofibrillary tangles are intraneuronal lesions that are composed of hyperphosphorylated and insoluble accumulations of the microtubule-associated protein, tau. These accumulations are a histopathological feature not only of AD, but also of many other neurodegenerative diseases, which are collectively known as tauopathies. Tauopathies include, e.g., Alzheimer's disease (AD), Pick's disease (PiD), progressive supranuclear palsy (PSP), corticobasal degeneration (CBD), and frontotemporal lobar degeneration (FTLD). In human tauopathies, pathology progresses from one brain region to another in disease-specific patterns, the underlying mechanism of which is not yet clear.

Tau pathology thus is involved in and may be a cause of many tauopathies. In its normal form, tau is a highly soluble microtubule-associated protein expressed predominantly in neuronal axons that binds and promotes the assembly and stability of microtubules. The tau protein contains many potential phosphorylation sites and the regulated phosphorylation and dephosphorylation of several of these sites has been shown to affect its interaction with tubulin and cytoskeleton function. Hyperphosphorylation of tau is thought to lead to microtubule dissociation and to an assembly of the normally disordered, highly soluble protein into β sheet-rich fibrils, or tau aggregates, also called paired helical filaments (PHFs), that make up NFTs and that can be visualized within dystrophic neurites and cell bodies. While the initial step of tau fibrillization is energetically unfavorable, once nuclei are formed, they rapidly recruit tau monomer and convert into thermodynamically stable aggregates. Subsequently, these aggregates can undergo fragmentation generating more fibril ends that are capable of recruiting tau monomers and converting them into de novo fibrils. This process is in most general terms referred to as "seeding". The amount of tau pathology correlates with progressive neuronal dysfunction, synaptic loss, and functional decline in humans and transgenic mouse models. Passive and active immunizations against tau have been analyzed in mice using several different mouse models, including different phospho-tau peptides for active immunizations and anti-tau antibodies for passive immunotherapy. Passive immunization with well-characterized anti-tau antibodies which react with phosphorylated Ser396 and Ser404 of the hyperphoshorylated tau protein at an early pathologic conformational epitope on tau, confirmed the results seen in active immunization studies. Mice treated with these antibodies showed marked reductions in tau pathology, which was measured by biochemical methods and histology, as well as a significant delay in loss of motor-function decline which was assessed in behavioral testings (Boutajangout A, et al, J Neurochem. 2011; 118(4): 658-667, Chai X, et al. J Biol Chem. 2011; 286(39):34457-34467.)

Currently the most prevalent medical approach for AD is to provide symptomatic therapy which is not efficacious even after several years of treatment. New therapeutic approaches and strategies for AD need to go beyond the treatment of symptoms to prevent cognitive decline and counteract the fundamental pathological processes of the disease. In particular, there is a need for the development of molecules that either alone or in combination with other AD-targeted drugs interfere with at least some of the earliest stages of the disease. Such molecules would provide new, advantageous options in the early diagnosis (which could itself improve treatment outcomes), prevention, and treatment of AD and other tauopathies.

SUMMARY OF THE INVENTION

The present invention provides novel binding molecules, in particular human binding molecules, e.g. human antibodies or antigen-binding fragments thereof, capable of specifically binding to tau paired helical filaments (PHFs), and which are capable of inhibiting spreading of tau aggregation and/or mediating uptake and degradation of tau aggregates by microglia.

In a preferred embodiment, the binding molecules according to the present invention are selected from the group consisting of:

a binding molecule comprising a heavy chain CDR1 comprising the amino acid sequence of SEQ ID NO: 1, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 10, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 11, a heavy chain CDR3 comprising the amino acid sequence of SEQ ID NO: 3, a light chain CDR1 comprising the amino acid sequence of SEQ ID NO: 10, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 12, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6; and a binding molecule comprising a heavy chain CDR1 comprising the amino acid sequence of SEQ ID NO: 12, a heavy chain CDR2 comprising the amino acid sequence of SEQ ID NO: 11, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6.

In certain embodiments, the binding molecules are capable of binding tau paired helical filaments (PHFs) in vitro and/or ex-vivo In certain embodiments, the binding molecules are capable of inhibiting the spreading of tau aggregation in vitro.

In certain embodiments, the binding molecules are capable of binding tau paired helical filaments (PHFs) and mediate their uptake by microglia in vitro.

In certain embodiments the binding molecules comprise a heavy chain variable region comprising an amino acid sequence selected from the group consisting of SEQ ID NO: 15, 16, 18, 19 and 20, and a light chain variable region selected from the group consisting of SEQ ID NO: 14 and 17.

In certain embodiments, the binding molecules of the present invention are selected from the group consisting of:
a binding molecule comprising a heavy chain variable region comprising the amino acid sequence of SEQ ID NO: 15 and a light chain variable region comprising the amino acid sequence of SEQ ID NO: 14;
a binding molecule comprising a heavy chain variable region comprising the amino acid sequence of SEQ ID NO: 16 and a light chain variable region comprising the amino acid sequence of SEQ ID NO: 14;
a binding molecule comprising a heavy chain variable region comprising the amino acid sequence of SEQ ID NO: 16 and a light chain variable region comprising the amino acid sequence of SEQ ID NO: 17;
a binding molecule comprising a heavy chain variable region comprising the amino acid sequence of SEQ ID NO: 18 and a light chain variable region comprising the amino acid sequence of SEQ ID NO: 17;
a binding molecule comprising a heavy chain variable region comprising the amino acid sequence of SEQ ID NO: 19 and a light chain variable region comprising the amino acid sequence of SEQ ID NO: 14; and
a binding molecule comprising a heavy chain variable region comprising the amino acid sequence of SEQ ID NO: 20 and a light chain variable region comprising the amino acid sequence of SEQ ID NO: 14.

Preferably, the binding molecules according to the present invention are human monoclonal antibodies, or antigen-binding fragments thereof.

In certain embodiments, the binding molecules are human monoclonal IgG antibodies, preferably IgG1 antibodies.

The invention also pertains to immunoconjugates, comprising at least one binding molecule according to the present invention and further comprising at least one tag.

Another aspect of the present invention relates to nucleic acid molecules encoding the binding molecules according to the present invention.

The binding molecules, immunoconjugates and/or nucleic acid molecules of the invention are suitable for use as a medicament, preferably for use in the diagnosis, prophylaxis and/or treatment of tauopathies, including but not limited to Alzheimer's disease (AD).

The invention also pertains to functional variants of the binding molecules according to the present invention.

The invention also pertains to pharmaceutical compositions comprising a binding molecule according to the present invention and/or an immunoconjugate, and a pharmaceutically acceptable carrier or excipient.

DEFINITIONS

Figure 1:
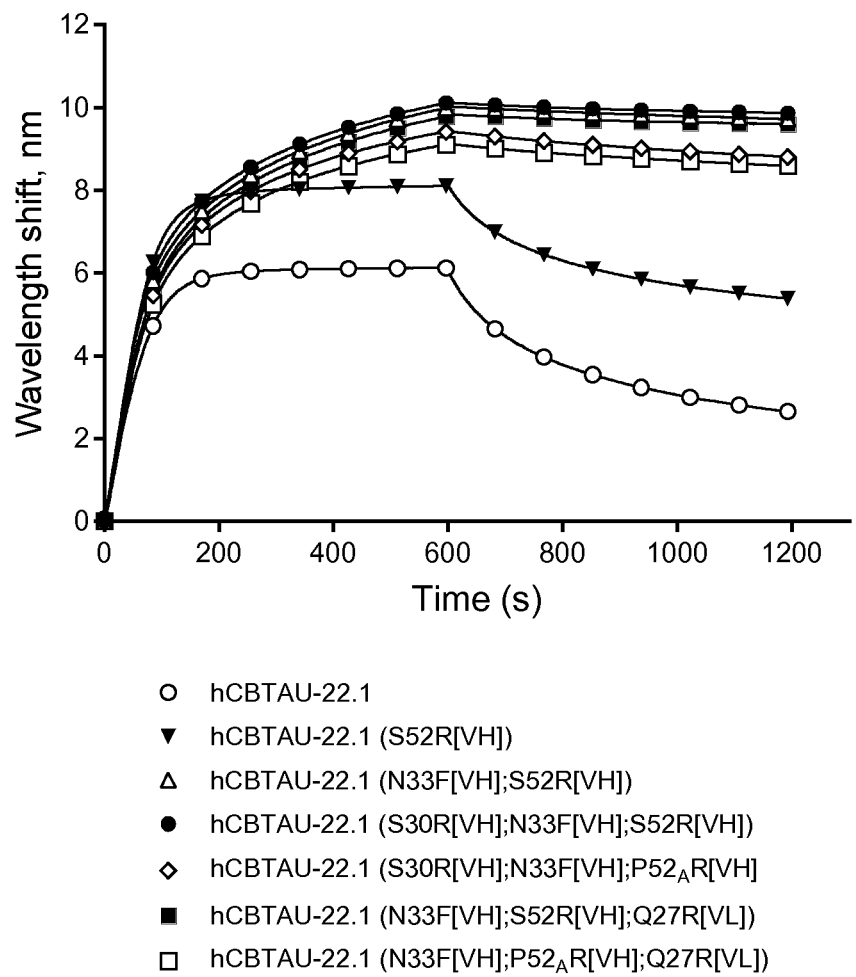
FIG. 1: Assessment of affinity by Biolayer Interferometry (Octet).

The term "binding molecule", as used herein includes all immunoglobulin classes and subclasses known in the art. Depending on the amino acid sequence of the constant domain of their heavy chains binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

As used throughout the present invention, the term "antigen-binding fragments" means a portion of an intact binding molecule, such as an antibody. Examples of antibody fragments include Fab, Fab', F(ab')2 and Fv fragments, CDR, antigen-binding site, heavy or light chain variable region, diabodies, triabodies single chain antibody molecules(scFv) and multispecific antibodies formed from at least two intact antibodies or fragments thereof or (poly) peptides that contain at least a fragment of an immunoglobin that is sufficient to confer antigen binding to the (poly) peptide, etc. An antigen-binding fragment may comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the antibody. The antigen-binding fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference. An antibody or antigen-binding fragment thereof may have one or more binding sites. If there is more than one binding site, the binding sites may be identical to one another or they may be different.

An immunoglobulin light or heavy chain variable region consists of a "framework" region interrupted by "antigen-binding sites". The antigen-binding sites are defined using various terms as follows: (i) Complementarity Determining Regions (CDRs) are based on sequence variability (Wu and Kabat J Exp Med 132:211-50, 1970). Generally, the antigen binding site has three CDRs in each variable region (HCDR1, HCDR2 and HCDR3 in heavy chain variable region (VH) and LCDR1, LCDR2 and LCDR3 in light chain variable region (VL)) (Kabat et al., Sequences of Proteins of Immunological Interest, 5th Ed. Public Health Service, National Institutes of Health, Bethesda, Md., 1991). (ii) The term "hypervariable region", "HVR", or "HV" refers to the regions of an antibody variable domain which are hypervariable in structure as defined by Chothia and Lesk (Chothia and Lesk J Mol Biol 96:901-17, 1987). Generally, the antigen-binding site has three hypervariable regions in each VH (H1, H2, H3) and VL (L1, L2, L3). Chothia and Lesk refer to structurally conserved HVs as "canonical structures". Numbering systems as well as annotation of CDRs and HVs have recently been revised by Abhinandan and Martin (Abhinandan and Martin Mol Immunol 45:3832-9, 2008). (iii) Another definition of the regions that form the antigen-binding site has been proposed by Lefranc (Lefranc, et al. Dev Camp Immunol 27:55-77, 2003) based on the comparison of V domains from immunoglobulins and T-cell receptors. The International ImMunoGeneTics (IMGT) database (http://www imgt_org) provides a standardized numbering and definition of these regions. The correspondence between CDRs, HVs and IMGT delineations is described in Lefranc et al. The antigen-binding site can also be delineated based on Specificity Determining Residue Usage (SDRU) (Almagro J Mol Recognit 17:132-43, 2004), where Specificity Determining Residues (SDR), refers to amino acid residues of an immunoglobulin that are directly involved in antigen contact.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply every antibody of the present invention. For example, depending on the position of the first CDR the following CDRs might be shifted in either direction.

"Framework" or "framework sequence" are the remaining sequences within the variable region of an antibody other than those defined to be antigen-binding site sequences. Because the exact definition of an antigen-binding site can be determined by various delineations as described above, the exact framework sequence depends on the definition of the antigen-binding site.

The term "monoclonal antibody" (mAb) as used herein means an antibody (or antibody fragment) obtained from a population of substantially homogeneous antibodies. Monoclonal antibodies are highly specific, typically being directed against a single antigenic determinant.

The term "specifically binding", or "specifically recognize", as used herein, in reference to the interaction of an antibody and its binding partner, e.g. an antigen, means that the interaction is dependent upon the presence of a particular amino acid sequence or structure, e.g. an antigenic determinant or epitope, on the binding partner. In other words, the antibody preferentially binds or recognizes the binding partner even when the binding partner is present in a mixture of other molecules or organisms. The binding may be mediated by covalent or noncovalent interactions or a combination of both. In yet other words, the term "specifically binding" or "specifically recognizes" means that the antibody is specifically immunoreactive with an antigenic determinant or epitope and is not immunoreactive with other antigenic determinants or epitopes. An antibody that (immuno) specifically binds to an antigen may bind to other peptides or polypeptides with lower affinity as determined by, e.g., radioimmunoassays (RIA), enzyme-linked immunosorbent assays (ELISA), BIACORE, or other assays known in the art. Antibodies or fragments thereof that specifically bind to an antigen may be cross-reactive with related antigens, carrying the same epitope. Preferably, antibodies or fragments thereof that specifically bind to an antigen do not cross-react with other antigens.

The term "epitope" as used herein means that part of the antigen that is contacted by the CDR loops of antibody. A "structural epitope" comprises about 15-22 contact residues on the the antigen surface and involves many amino acid residues that make contact with a large group of residues on CDRs collectively referred to as the paratope of antibody. Direct contact between epitope and paratope residues is established through electrostatic forces such as hydrogen bonds, salt bridges, van der Waals forces of hydrophobic surfaces and shape complementarity. The interface has also bound water molecules or other co-factors that contribute to the specificity and affinity of antigen-antibody interactions. The binding energy of an antigen-antibody complex is primarily mediated by a small subset of contact residues in the epitope-paratope interface. These "energetic residues" are often located in the center of the epitope-paratope interface and make up the functional epitope. Contact residues in the periphery of the interface make generally minor contributions to the binding energy; their replacements have frequently little effect on the binding with antigen. Thus, the binding or functional activity of an epitope involves a small subset of energetic residues centrally located in the structural epitope and contacted by the specificity-determining CDRs. The assignment of a functional epitope on an antigenic protein can be made using several methods including Alanine scan mutagenesis or by solving the crystal structure of the antigen with the antibody. An epitope can be linear in nature or can be a discontinuous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in 3-dimensional space. For discontinuous epitopes, it may be possible to obtain binding of one or more linear peptides with decreased affinity to a so-called partial epitope, e. g. dispersed at different regions of the protein sequence (Cragg, M. S. (2011) Blood 118 (2): 219-20).

As used herein, the term "affinity" refers to a measure of the strength of the binding of an individual epitope or partial epitope with the CDRs of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W.H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., KD, IC50, are preferably made with standardized solutions of antibody and antigen, and a standardized buffer.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid molecule" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

As used herein, the terms "treat" or "treatment" refer to both therapeutic treatment and prophylactic or preventative measures, wherein the object is to prevent or slow down (lessen) an undesired physiological change or disorder, such as the development of Parkinsonism or Alzheimer's Disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented. A "medicament" as used herein, is an agent used in the treatment of an undesirable physiological change or disorder.

By "subject" or "individual" or "animal" or "patient" or "mammal," is meant any subject, particularly a mammalian subject, e.g., a human patient, for whom diagnosis, prognosis, prevention, or therapy is desired.

DETAILED DESCRIPTION OF THE INVENTION

In a first aspect, the present invention provides binding molecules, e.g. antibodies and/or antigen-binding fragments thereof, that are capable of specifically binding to tau paired helical filaments (PHFs) and that are capable of inhibiting spreading of tau aggregation and/or mediating mediate uptake of tau aggregates by microglia, wherein the binding molecules are selected from the group consisting of:

a binding molecule comprising a heavy chain CDR1 comprising the amino acid sequence of SEQ ID NO: 1, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 10, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 11, a heavy chain CDR3 comprising the amino acid sequence of SEQ ID NO: 3, a light chain CDR1 comprising the amino acid sequence of SEQ ID NO: 10, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 12, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6; and a binding molecule comprising a heavy chain CDR1 comprising the amino acid sequence of SEQ ID NO: 12, a heavy chain CDR2 comprising the amino acid sequence of SEQ ID NO: 11, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6.

In certain embodiments, the binding molecules are capable of binding tau PHFs in vitro and/or ex-vivo.

In certain embodiments, the binding molecules are capable of inhibiting the spreading of tau aggregation in vitro.

In certain embodiments, the binding molecules are capable of binding tau paired helical filaments (PHFs), and mediate their uptake by microglia in vitro.

In certain embodiments the binding molecules comprise a heavy chain variable region comprising an amino acid sequence selected from the group consisting of SEQ ID NO: 15, 16, 18, 19 and 20, and a light chain variable region selected from the group consisting of SEQ ID NO: 14 and 17.

In certain embodiments, the binding molecules of the present invention are selected from the group consisting of:

a binding molecule comprising a heavy chain variable region comprising the amino acid sequence of SEQ ID NO: 15 and a light chain variable region comprising the amino acid sequence of SEQ ID NO: 14;

a binding molecule comprising a heavy chain variable region comprising the amino acid sequence of SEQ ID NO: 16 and a light chain variable region comprising the amino acid sequence of SEQ ID NO: 14;

a binding molecule comprising a heavy chain variable region comprising the amino acid sequence of SEQ ID NO: 16 and a light chain variable region comprising the amino acid sequence of SEQ ID NO: 17;

a binding molecule comprising a heavy chain variable region comprising the amino acid sequence of SEQ ID NO: 18 and a light chain variable region comprising the amino acid sequence of SEQ ID NO: 17;

a binding molecule comprising a heavy chain variable region comprising the amino acid sequence of SEQ ID NO: 19 and a light chain variable region comprising the amino acid sequence of SEQ ID NO: 14; and a binding molecule comprising a heavy chain variable region comprising the amino acid sequence of SEQ ID NO: 20 and a light chain variable region comprising the amino acid sequence of SEQ ID NO: 14.

In certain embodiments, the binding molecules are human monoclonal IgG antibodies, preferably IgG1 antibodies.

According to the present invention, novel binding molecules are provided that specifically bind tau PHF with very high affinity and that are capable of inhibiting the propagation of PHF-like aggregates. In certain embodiments, the binding molecules are capable of binding tau PHFs and promote their uptake by microglia via an Fc mediated mechanism.

In certain embodiments, the binding molecules specifically bind tau with an affinity of 250 nM or less, preferably 100 nM or less, preferably 50 nM or less, more preferably 25 nM or less, even more preferably 10 nM or less, most preferably 1 nM or less.

Tau is an abundant central and peripheral nervous system protein having multiple well-known isoforms. In the human central nervous system (CNS), six major tau isoforms ranging in size from 352 to 441 exist due to alternative splicing (Hanger, et al. Trends Mol Med 15:112-9, 2009). These isoforms differ from each other by the regulated inclusion of 0, 1 or 2 N-terminal acidic inserts (0N, 1N or 2N), and 3 or 4 tandemly arranged microtubule-binding repeats (3R or 4R), and are referred to as 0N3R, 1N3R, 2N3R, 0N4R, 1N4R and 2N4R. The recombinant tau as used herein refers to the tau isoform of SEQ ID NO: 9. The tau protein can be recombinantly expressed in high quantities, for example, in E. coli, baculovirus, mammalian or cell-free systems. Recombinant tau may be recombinantly expressed and purified using standard methods (e.g. Barghorn, et al 2005, Meth Mol Biol 35-51).

In an embodiment, the binding molecules of the invention, such as antibodies or antigen-binding fragments thereof, specifically bind to a phosphorylated tau peptide comprising the amino acid sequence of SEQ ID NO: 9.

Tau binds microtubules and regulates transport of cargo through cells, a process that can be modulated by tau phosphorylation which occurs at many of the 79 potential serine (Ser) and threonine (Thr) phosphorylation sites. Tau is highly phosphorylated during brain development. The degree of phosphorylation declines in adulthood. Some of the phosphorylation sites are located within the microtubule binding domains of tau, and it has been shown that an increase of tau phosphorylation negatively regulates the binding of microtubules. For example, Ser262 and Ser396, which lie within or adjacent to microtubule binding motifs, are hyperphosphorylated in the tau proteins of the abnormal paired helical filaments (PHFs), a major component of the neurofibrillary tangles (NFTs) in the brain of AD patients.

The term "paired helical filament-tau" or "PHF-tau" as used herein refers to well-known tau aggregates which make up the pathological structures called neurofibrillary tangles (NFT), first described by Alzheimer in the brain of dementia patient. Their presence is also found in numerous other diseases known as tauopathies. Aggregates of tau thus can be observed as the main component of neurofibrillary tangles (NFT) in e.g. Alzheimer's disease (AD), Frontotemporal dementias, supranuclear palsy, Pick's disease, Argyrophilic grain disease (AGD), corticobasal degeneration, FTDP-17, Parkinson's disease, Dementia pugilistica (Reviewed in Gendron and Petrucelli, Mol. Neurodegener. 4:13 (2009)).

The term "neurofibrillary tangle" (NFT) refers to the pathological structures first described by Alzheimer in the brain of dementia patient. NFT are composed of orderly arranged paired helical filaments of hyperphosphorylated tau protein that are most commonly known as a primary marker of Alzheimer's Disease.

Physiological tau protein stabilizes microtubules in neurons. Pathological phosphorylation leads to abnormal tau localization and aggregation, which causes destabilization of microtubules and impaired cellular transport. Aggregated tau is neurotoxic in vitro (Khlistunova et al., J. Biol. Chem. 281 (2006), 1205-1214). The exact neurotoxic species remains unclear, however, as do the mechanism(s) by which they lead to neuronal death.

According to the invention, novel binding molecules are provided that specifically bind to tau PHFs and that are capable of inhibiting the spreading of tau aggregates and/or of mediating their uptake and possible degradation by microglia. Thus, the binding molecules of the invention could serve as possible therapeutic reagents that prevent formation of tau pathology, as biomarkers to assess risks of developing AD and/or as reagents used to capture biomarkers that assess the risk of developing AD.

The binding molecules of the invention can be intact immunoglobulin molecules such as monoclonal antibodies, or the binding molecules can be antigen-binding fragments thereof, including, but not limited to, heavy and light chain variable regions, Fab, F(ab'), F(ab')2, Fv, dAb, Fd, complementarity determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to tau.

In a preferred embodiment the binding molecules of the invention are human monoclonal antibodies, and/or antigen-binding fragments thereof. The binding molecules may also be nanobodies, alphabodies, affibodies, FN3-domain scaffolds and other scaffolds based on domains in (human) repeat proteins, like Adnectins, Anticalins, Darpins, Centyrins, etc, or other scaffolds comprising epitope binding sequences.

In certain embodiments, the antibodies are chimeric antibodies.

In certain embodiments, the antibodies are chimeric antibodies comprising a heavy chain variable region comprising the amino acid sequence of SEQ ID NO: 15 and a light chain variable region comprising the amino acid sequence of SEQ ID NO: 14; a heavy chain variable region comprising the amino acid sequence of SEQ ID NO: 16 and a light chain variable region comprising the amino acid sequence of SEQ ID NO: 14; a heavy chain variable region comprising the amino acid sequence of SEQ ID NO: 16 and a light chain variable region comprising the amino acid sequence of SEQ ID NO: 17; a heavy chain variable region comprising the amino acid sequence of SEQ ID NO: 18 and a light chain variable region comprising the amino acid sequence of SEQ ID NO: 17; a heavy chain variable region comprising the amino acid sequence of SEQ ID NO: 19 and a light chain variable region comprising the amino acid sequence of SEQ ID NO: 14; or a heavy chain variable region comprising the amino acid sequence of SEQ ID NO: 20 and a light chain variable region comprising the amino acid sequence of SEQ ID NO: 14, and a recombinant constant region of a human IgG1.

In certain embodiments, the antibodies are chimeric antibodies comprising an antigen binding variable region from a human antibody which binds specifically to tau, and a recombinant constant region of a human IgG1, wherein the constant region of the chimeric antibody differs from the constant region of the human antibody.

In certain embodiments, the antibodies are chimeric antibodies comprising heavy and light chain variable regions from a human antibody, and recombinant human IgG 1 heavy and light chain constant regions.

The present invention also relates to pharmaceutical compositions comprising at least one binding molecule according to the invention, and at least a pharmaceutically acceptable excipient.

In yet a further aspect, the invention provides immunoconjugates, i.e. molecules comprising at least one binding molecule as defined herein and further comprising at least one tag. The tag(s) can be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan. The tags of the immunoconjugates of the present invention may be therapeutic agents, but they can also be detectable moieties/agents. Tags suitable in therapy and/or prevention may be toxins or functional parts thereof, antibiotics, enzymes, other binding molecules that enhance phagocytosis or immune stimulation. Immunoconjugates comprising a detectable agent can be used diagnostically to, for example, assess if a subject is in the process of developing AD. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., phagocytosis assays), Western blotting applications, etc. Suitable labels for the detection/analysis/diagnosis techniques and/or methods known in the art are well within the reach of the skilled artisan.

It is another aspect of the present invention to provide nucleic acid molecules encoding at least a binding molecule, functional variant or immunoconjugate according to the invention. Such nucleic acid molecules can e.g. be used as intermediates for cloning purposes. In a preferred embodiment, the nucleic acid molecules are isolated or purified. The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

It is another aspect of the invention to provide polynucleotides, e.g. vectors, comprising one or more nucleic acid molecules according to the present invention. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses. Vectors can be used for cloning and/or for expression of the binding molecules of the invention and might even be used for gene therapy purposes. Vectors comprising one or more nucleic acid molecules according to the invention operably linked to one or more expressionregulating nucleic acid molecules are also covered by the present invention. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional aspect of the present invention. Preferably, the hosts are host cells. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorphs*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, NSO cells or Bowes melanoma cells are preferred in the present invention. Mammalian cells provide expressed proteins with posttranslational modifications that are most similar to natural molecules of mammalian origin. Since the present invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, said host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application "PER.C6 cells" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403 the disclosure of which is incorporated herein by reference in its entirety.

A method of producing a binding molecule according to the invention is an additional aspect of the invention. In certain embodiments, the method comprises the steps of a) culturing a host according to the invention under conditions conducive to the expression of the binding molecule, and b) optionally, recovering the expressed binding molecule. The expressed binding molecules can be recovered from the cell free extract, but preferably they are recovered from the culture medium. The above method of producing can also be used to make functional variants of the binding molecules and/or immunoconjugates of the present invention. Methods to recover proteins, such as binding molecules, from cell free extracts or culture medium are well known to the man skilled in the art. Binding molecules, functional variants and/or immunoconjugates obtainable by the above-described method are also a part of the present invention.

Alternatively, next to the expression in hosts, such as host cells, the binding molecules and immunoconjugates of the invention can be produced synthetically by conventional peptide synthesizers or in cell-free translation systems using RNA nucleic acid derived from DNA molecules according to the invention. Binding molecules and immunoconjugates as obtainable by the above described synthetic production methods or cell-free translation systems are also a part of the present invention.

In yet a further aspect, the invention provides compositions comprising at least a binding molecule, preferably a human monoclonal antibody, according to the invention, at least a functional variant thereof, at least an immunoconjugate according to the invention and/or a combination thereof. In addition to that, the compositions may comprise, inter alia, stabilizing molecules, such as albumin or polyethylene glycol, or salts. Preferably, the salts used are salts that retain the desired biological activity of the binding molecules and do not impart any undesired toxicological effects. If necessary, the human binding molecules of the invention may be coated in or on a material to protect them from the action of acids or other natural or non-natural conditions that may inactivate the binding molecules.

In yet a further aspect, the invention provides compositions comprising at least a nucleic acid molecule as defined in the present invention. The compositions may comprise aqueous solutions such as aqueous solutions containing salts (e.g., NaCl or salts as described above), detergents (e.g., SDS) and/or other suitable components.

Furthermore, the present invention pertains to pharmaceutical compositions comprising at least a binding molecule, such as a human monoclonal antibody, of the invention (or functional fragment or variant thereof), at least an immunoconjugate according to the invention, at least a composition according to the invention, or combinations thereof. The pharmaceutical composition of the invention further comprises at least one pharmaceutically acceptable excipient or carrier. Pharmaceutically acceptable excipients and carriers are well known to the skilled person.

In certain embodiments, the pharmaceutical composition comprises at least one other prophylactic and/or therapeutic agent. Such agents can be binding molecules, small molecules, organic or inorganic compounds, enzymes, polynucleotide sequences, etc. These can be used in combination with the binding molecules of the invention. "In combination" herein means simultaneously, as separate formulations, or as one single combined formulation, or according to a sequential administration regimen as separate formulations, in any order.

In certain embodiments, the binding molecules are for use in inhibiting and/or prevention tau protein aggregation.

In certain embodiments, the binding molecules are for use as a medicament, and preferably for use in the diagnostic, therapeutic and/or prophylactic treatment of neurodegenerative diseases, such as AD. Thus, the binding molecules of the invention or fragments thereof can be used to treat, reduce or prevent symptoms in patients having a neurodegenerative disease that involves accumulation of pathological tau or tau aggregation within the brain, such as patients suffering from AD as well as any other tauopathy or other tau-related pathologies in which tau may be overexpressed. While not wishing to be bound by any particular theory, the binding molecules of the invention may exert their beneficial effect by reducing or eliminating pathological tau or tau aggregation and hence the amount of PHF-tau in the brain. The binding molecules of the invention may be used to treat an animal patient belonging to any classification. Examples of such animals include mammals such as humans, rodents, dogs, cats and farm animals.

Another embodiment of the invention is a method for inhibiting and/or preventing the spreading of tau protein aggregation.

Another embodiment of the invention is a method of treating or reducing symptoms of a neurodegenerative disease that involves aggregation of tau in a patient comprising administering to the patient a therapeutically effective amount of the binding molecule of the invention for a time sufficient to treat or reduce symptoms of the neurodegenerative disease. In any of the embodiments above, the neurodegenerative disease that involves aggregation of tau is a tauopathy. As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-StrausslerScheinker disease, Hallervorden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, nonguanamian motor neuron disease with neurofibrillary tangles, postencephalitic parkinsonism, and chronic traumatic encephalopathy, such as dementia pugulistica (boxing disease). (Morris, et al. Neuron 70:410-26, 2011).

A tauopathy-related behavioral phenotype includes cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes, PS 1 and PS2, and ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and A□ 42 levels. Elevated tau and decreased A□ 42 levels signify the presence of AD. Individuals suffering from AD can also be diagnosed by AD and Related Disorders Association criteria.

Anti-tau binding molecules of the invention are suitable both as therapeutic and prophylactic agents for treating or preventing neurodegenerative diseases that involves accumulation of pathological aggregation of tau, such as AD or other tauopathies or tau-associated ailments. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions or medicaments are administered to a patient susceptible to, or otherwise at risk of, AD or other ailment involving tau, in an amount sufficient to eliminate or reduce the risk, lessen the severity, or delay the outset of the disease, including biochemical, histologic and/or behavioral symptoms of a disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic may reduce or eliminate mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, compositions or medicaments are usually administered in several dosages until a sufficient immune response has been achieved.

Anti-tau binding molecules or fragments thereof of the invention may be administered in combination with other agents that are effective for treatment of related neurodegenerative diseases. In the case of AD, antibodies of the invention may be administered in combination with agents that reduce or prevent the deposition of amyloid beta (Aβ). It is possible that PHF-tau and Aβ pathologies are synergistic. Therefore, combination therapy targeting the clearance of both PHF-tau and Aβ-related pathologies at the same time may be more effective than targeting each individually.

In the case of Parkinson's Disease and related neurodegenerative diseases, immune modulation to clear aggregated forms of the a-synuclein protein is also an emerging therapy. A combination therapy which targets the clearance of both tau and β-synuclein proteins simultaneously may be more effective than targeting either protein individually. In the methods of the invention, the "therapeutically effective amount" of the binding molecule, e.g. antibody or antigen-binding fragment thereof, in the treatment or ameliorating symptoms of a tauopathy can be determined by standard research techniques. For example, the dosage of the antibody can be determined by administering the agent to relevant animal models well known in the art.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The mode of administration for therapeutic use of the binding molecules of the invention may be any suitable route that delivers the agent to the host. Pharmaceutical compositions of these binding molecules are useful for parenteral administration, e.g., intradermal, intramuscular, intraperitoneal, intravenous, subcutaneous, intranasal or intracranial or they can be administered into the cerebrospinal fluid of the brain or spine.

The treatment may be given in a single dose schedule, or as a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease. Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of an antibody of the invention. Similarly, a pharmaceutical composition of the invention for intravenous infusion could be made up to contain about 250 ml of sterile Ringer's solution, and about 1 mg to about 30 mg or about 5 mg to about 25 mg of an antibody of the invention. Actual methods for preparing parenterally administrable compositions are well known and are described in more detail in, for example, "Remington's Pharmaceutical Science", 15th ed., Mack Publishing Company, Easton, Pa.

The binding molecules of the invention can be lyophilized for storage and reconstituted in a suitable carrier prior to use. This technique has been shown to be effective with antibody and other protein preparations and art-known lyophilization and reconstitution techniques can be employed.

In certain embodiments, the binding molecules may be used in methods of diagnosing AD or other tauopathy in a subject. This method involves detecting, in the subject, the presence of tau using a diagnostic reagent such as an antibody or a fragment thereof of the present invention. Tau may be detected in a biological sample from a subject (e.g., blood, urine, cerebral spinal fluid) by contacting the biological sample with the diagnostic antibody reagent, and detecting binding of the diagnostic antibody reagent to PHF-tau in the sample from the subject. Assays for carrying out the detection include well known methods such as ELISA, immunohistochemistry, western blot, or in vivo imaging.

Diagnosis may be performed by comparing the number, size, and/or intensity of labeled tau, tau accumulation, tau aggregates, and/or neurofibrillary tangles in a sample from the subject or in the subject, to corresponding baseline values. The baseline values can represent the mean levels in a population of undiseased individuals. Baseline values can also represent previous levels determined in the same subject.

The diagnostic methods described above can also be used to monitor a subject's response to therapy by detecting the presence of tau in a subject before, during or after the treatment. A change in values relative to baseline signals a response to treatment. Values can also change temporarily in biological fluids as pathological tau is being cleared from the brain.

The present invention is further directed to a kit for performing the above described diagnostic and monitoring methods. Typically, such kits contain a diagnostic reagent such as the binding molecules of the invention, and optionally a detectable label. The diagnostic binding molecule, e.g. antibody, itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring tau in a biological sample, the antibodies of the kit may be supplied pre-bound to a solid phase, such as to the wells of a microtiter dish.

The invention is further illustrated in the Examples, which are not intended to limit the invention in any way.

EXAMPLES

Example 1

Preparation of Novel Antibodies of Invention

Human IgG1 antibodies were constructed by cloning the heavy (VH) and light (VL) chain variable regions into a single expression vector containing IgG constant regions. Plasmids encoding the sequences corresponding to human anti-tau mAbs were transiently transfected in human embryonic kidney 293-derived Expi293F™ cells (Thermo Fisher) and 7 days post transfection, the expressed antibodies were purified from the culture medium by MabSelect SuRe (GE Healthcare) Protein A affinity chromatography. IgGs were eluted from the column with 100 mM sodium citrate buffer, pH 3.5 which was immediately buffer exchanged into PBS, pH 7.4 using a self-packed Sephadex G-25 column (GE Healthcare). Each antibody was quality controlled by SDS page and size exclusion chromatography coupled with multi angle light scattering (SEC-MALS) and was further confirmed for reactivity to cognate tau peptide by Octet biolayer interferometry.

Example 2

Octet Biolayer Interferometry Based Association and Dissociation Profiles of the Antibodies to the Cognate Tau Peptide V1089-24

The tau peptide V1089-24, comprising the amino acid sequence $^{412}$SSTGSIDMVDpSPOLATLA$^{429}$ (SEQ ID NO: 9), was bound via N-terminal biotin to a streptavidin biosensor. Association (0-600s) was followed upon immersing the sensor in solution containing the antibodies according to the invention (100 nM), whereas dissociation (600-1200 s) was followed by moving the sensor containing the protein complex into kinetic buffer. The buffer used for these experiments was obtained by diluting 10 fold the 10× 'Pall ForteBio's Kinetics Buffer' in PBS. Improvement in affinity is confirmed by larger shift in the wavelength (nm) and/or slower dissociation kinetics.

The results are shown in FIG. 1. As can be seen, the new binding molecules of the invention showed an improved binding profile to Tau peptide (SEQ ID NO: 9), as compared to the previously described antibody CBTAU 22.1 (WO2015/197823). This was manifested by significantly larger wavelength shifts upon association which indicate that a higher fraction of antibody molecules is bound to tau under steady-state conditions and slower dissociation kinetics which indicate that the new binding molecules stay attached to tau for considerably longer times.

Example 3

Ability of the Antibodies to Deplete Seeds from AD Brain Homogenates

Homogenates containing tau seeds were generated from cryopreserved human AD brain tissue. In immunodepletion assays the seeds were incubated with test antibody and removed from the solution with protein G Dynabeads. The depleted supernatant (named 'immunodepleted fraction') was tested for residual seeding capacity in the chromophore-K18-containing HEK293 cells and analyzed by Flow cytometry.

The FRET biosensor cells are HEK cells stably expressing K18/P301S-CFP and K18/P301S-YFP and were plated in 96-well plate format. Immunodepleted fractions were transfected in the cells by pre-mixing the fractions with Lipofectamine2000 to increase the assay window and incubated on the recipient FRET biosensor cells for 2 days after which the cells were trypsinized and the percentage of FRET positive cells was quantified by Flow cytometry. A FRET signal can only be measured when the K18 reporter proteins form aggregates and hence CFP and YFP are in close proximity. When exciting CFP, energy is transferred to the YFP resulting in YFP fluorescent light emission (Holmes et al, 2014, PNAS, 111, E4376-E4385)

Seeds:

Cryopreserved brain tissue was acquired from a biobank (Newcastle Brain Tissue Resource). Frozen brain tissue was homogenized with a Dounce homogenizer at 1000 rpm for 10 strokes in homogenization buffer (10 mM Tris (Gibco, cat #15567-027), 150 mM NaCl (Gibco, cat #24740-011), pH 7.4, filter: 0.22 µm+Complete mini EDTA-free protease inhibitors (Roche, cat #11 836 170 001)) to obtain a 10% w/v homogenate. The homogenate was centrifuged at 27.000×g, 10 min at 4° C. and supernatant was stored in aliquots at −80° C. until used as seed in the immunodepletion assay.

Assay Procedure:

660 nM Antibody dilutions were prepared in PBS (Sigma, cat #D8537) to obtain a final 300 nM concentration in the antibody-seed-bead mix described below. Seeds were diluted 1.3 fold in PBS to achieve a complete depletion at 300 nM antibody concentration and maintain a decent seeding window. Antibody and seed dilutions were mixed in a 1:1 ratio in a 96well PCR plate (Thermo Scientific AB-0600) and incubated until the beads were washed.

121.5 µl Protein-G DynaBeads suspension (Life Technologies; cat #10004D) was added in a 96-well PCR plate (Thermo Scientific AB-0600) per well and washed twice by pulling down the beads with a magnet (Life Technologies; cat #123.31D) to be able to remove the buffer from the beads and resuspend the beads in PBS with 0.01% Tween20 (Sigma, cat #P1379). Wash buffer was removed completely and 10 µl of PBS with 0.1% Tween20 was added to the beads in each well and 90 µl of the 1:1 antibody-seed mixture was added per well. The antibody-seed-bead mix should contain 0.01% Tween20 to prevent the beads from sticking to the plastic of the PCR plate.

The antibody-seed-bead mix was incubated over night at 4° C., rotating at 5 rpm. Next day, the condensation was removed from the lid by centrifugation at 3000 rpm for approximately 20 sec. The immunodepleted fractions were separated from the beads by pulling down the beads with the magnet and transferred to a new 96well PCR plate to be stored at −80° C. until tested on the FRET biosensor cells for remaining seeding capacity. The beads were washed twice like described above and were stored dry in the PCR plate at −20° C. Each condition was tested in duplicate.

Immunodepleted fractions were reversely transfected into the FRET biosensor cells: 10 µl immunodepleted fraction was added per well in 96well plate (poly D lysine pre-coated µclear plates; Greiner Bio-one, cat #655946). 10 µl Lipofectamine 2000 (Invitrogen, cat #11668-027) diluted 40 times in Opti-MEM (Gibco, cat #11058-021) was added and this mix was incubated for 10 minutes in the plate. Per well, 55.000 FRET biosensor cells were added in 1300 DMEM, high glucose, GlutaMAX™ Supplement, pyruvate (Gibco, cat #31966-021) supplemented with 10% (v/v) heat-inactivated fetal bovine serum (Biowest, cat #S1810-500) and 1% Penstrep (Sigma P4333). After a 2-day incubation at 37° C., cells were washed twice with PBS (Sigma, cat #D8537) before they were detached for 5 min at 37° C. with 50 0/well 0.05% Trypsin/EDTA (Gibco, cat #25300-054). Cells were resuspend by pipetting up and down repeatedly and checked for single cells visually with a microscope. 300/well FACS buffer (Hank's Balanced Salt Solution (Sigma, cat #H8264), 1 mM EDTA (Invitrogen, cat #15575-038), 1% FBS (Biowest, cat #S1810-500)) was added in polypropylene round bottom plate (MW384; Costar, cat #3657) to which 50 µl cell suspension was added. Cells were analyzed for FRET positivity by Flow cytometry.

Figure 2:
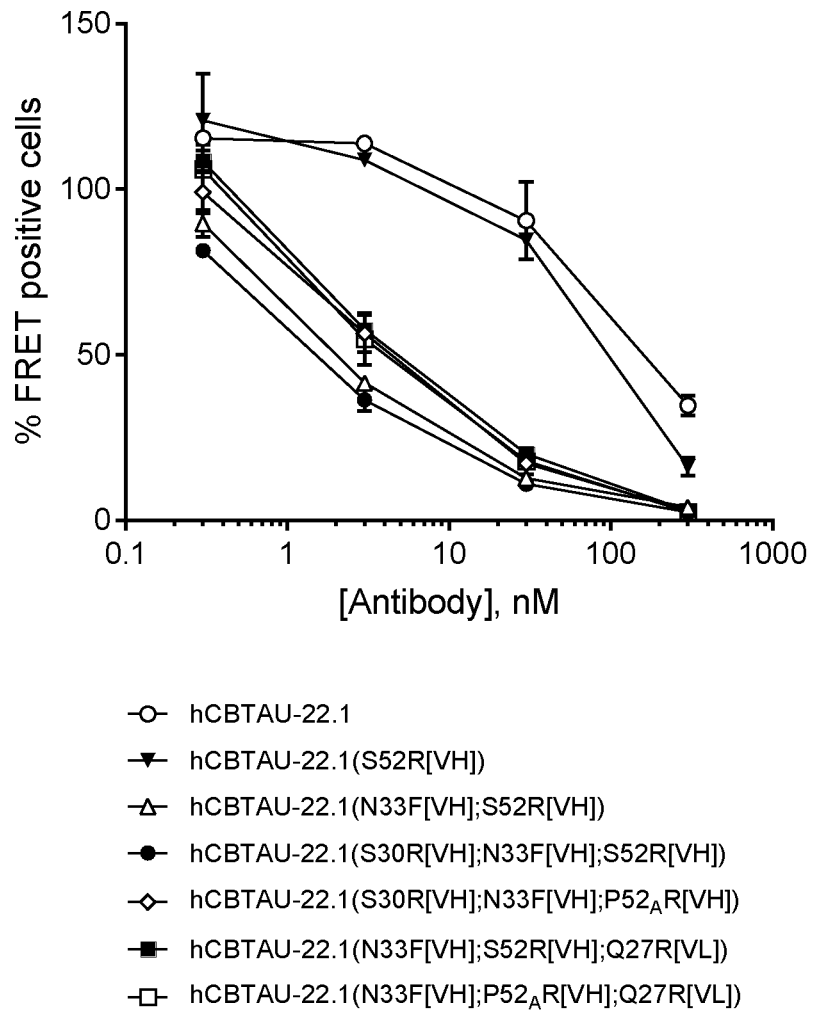
FIG. 2: Ability of the binding molecules of the invention to deplete seeds from AD brain homogenates.

As shown in FIG. 2, the previously described antibody CBTAU-22.1 is capable to deplete PHFs from AD brain in a dose dependent manner as reflected by a reduction of seeding efficiency to 30% of the initial value for the highest concentration of antibody used in this experiment. Surprisingly, the new antibodies of the invention show a significantly higher PHF depletion potency. This is reflected by a steeper dose dependence effect and by the fact that at the highest antibody concentration used in the experiment the seeding is virtually neutralized. These observations show that these antibodies have a tremendously increased ability to neutralize PHF seeds from AD brain than the parental molecule.

SEQUENCES

| Antibody | CDR1 (SEQ ID NO:) | CDR2 (SEQ ID NO:) | CDR3 (SEQ ID NO:) |
|---|---|---|---|
| CBTAU 22.1_HC | GYRFSDYN (1) | ISPNSGGT (2) | VRGHCDGTTCSRAY (3) |
| CBTAU_LC | QSLLHRSGHKY (4) | LGS (5) | MQTLQTPWT (6) |
| S52$_A$ R[VH]_HC | GYRFSDYN (1) | IRPNSGGT (7) | VRGHCDGTTCSRAY (3) |
| S52$_A$ R[VH]_LC | QSLLHRSGHKY (4) | LGS (5) | MQTLQTPWT (6) |
| N33F[VH]; S52$_A$ R[VH]_HC | GYRFSDYF (8) | IRPNSGGT (7) | VRGHCDGTTCSRAY (3) |
| N33F[VH]; S52$_A$ R[VH]_LC | QSLLHRSGHKY (4) | LGS (5) | MQTLQTPWT (6) |
| N33F[VH]; S52$_A$ R[VH]; Q27R [VL]_HC | GYRFSDYF (8) | IRPNSGGT (7) | VRGHCDGTTCSRAY (3) |
| N33F[VH]; S52$_A$ R[VH]; Q27R [VL]_LC | RSLLHRSGHKY (10) | LGS (5) | MQTLQTPWT (6) |
| N33F[VH]; P52$_A$R[VH]; Q27R[VL]_HC | GYRFSDYF (8) | ISRNSGGT (11) | VRGHCDGTTCSRAY (3) |
| N33F[VH]; P52$_A$R[VH]; Q27R[VL]_LC | RSLLHRSGHKY (10) | LGS (5) | MQTLQTPWT (6) |
| S30R[V_HC; N33F[VH]; S52$_A$ R[VH]_HC | GYRFRDYF (12) | IRPNSGGT (9) | VRGHCDGTTCSRAY (3) |
| S30R[VH]; N33F[VH]; S52$_A$ R[VH]_LC | QSLLHRSGHKY (4) | LGS (5) | MQTLQTPWT (6) |
| S30R[VH]; N33F[VH]; P52$_A$R[VH]_HC | GYRFRDYF (12) | ISRNSGGT (11) | VRGHCDGTTCSRAY (3) |
| S30R[VH]; N33F[VH]; P52$_A$R[VH]_LC | QSLLHRSGHKY (4) | LGS (5) | MQTLQTPWT (6) |

```
Heavy chain variable region CBTAU-22.1
                                                (SEQ ID NO: 13)
QVQLVQSGAEVKKPGAPVKVSCETSGYRFSDYNVHWVRQAPGQGPEWIGRISPNSGGT

KYAQKFQGRVTMTRDMSMNTAYMELSGLRSDDTAVYYCVRGHCDGTTCSRAYWGQ

GTLVTVSS

Light chain variable region CBTAU-22.1
                                                (SEQ ID NO: 14)
DVVMTQSPLSLPVTPGEPASISCRSSQSLLHRSGHKYLHWYLQRPGQSPQVLIYLGSNRA

SGVPDRFSGSGSGTDFTLKISRVEAEDVGLYYCMQTLQTPWTFGQGTKVEIK

Heavy chain variable region [S52R]
                                                (SEQ ID NO: 15)
QVQLVQSGAEVKKPGAPVKVSCETSGYRFSDYNVHWVRQAPGQGPEWIGRIRPNSGGT

KYAQKFQGRVTMTRDMSMNTAYMELSGLRSDDTAVYYCVRGHCDGTTCSRAYWGQ

GTLVTVSS

Light chain variable region [S52R]
                                                (SEQ ID NO: 14)
DVVMTQSPLSLPVTPGEPASISCRSSQSLLHRSGHKYLHWYLQRPGQSPQVLIYLGSNRA

SGVPDRFSGSGSGTDFTLKISRVEAEDVGLYYCMQTLQTPWTFGQGTKVEIK

Heavy chain variable region N33F[VH]; S52R[VH]
                                                (SEQ ID NO: 16)
QVQLVQSGAEVKKPGAPVKVSCETSGYRFSDYFVHWVRQAPGQGPEWIGRIRPNSGGT

KYAQKFQGRVTMTRDMSMNTAYMELSGLRSDDTAVYYCVRGHCDGTTCSRAYWGQ

GTLVTVSS
```

-continued

Light chain variable region N33F[VH]; S52R[VH]
(SEQ ID NO: 14)
DVVMTQSPLSLPVTPGEPASISCRSSQSLLHRSGHKYLHWYLQRPGQSPQVLIYLGSNRA

SGVPDRFSGSGSGTDFTLKISRVEAEDVGLYYCMQTLQTPWTFGQGTKVEIK

Heavy chain variable region N33F[VH]; S52R[VH]; Q27R[VL]
(SEQ ID NO: 16)
QVQLVQSGAEVKKPGAPVKVSCETSGYRFSDYFVHWVRQAPGQGPEWIGRIRPNSGGT

KYAQKFQGRVTMTRDMSMNTAYMELSGLRSDDTAVYYCVRGHCDGTTCSRAYWGQ

GTLVTVSS

Light chain variable region N33F[VH]; S52R[VH]; Q27R[VL]
(SEQ ID NO: 17)
DVVMTQSPLSLPVTPGEPASISCRSSRSLLHRSGHKYLHWYLQRPGQSPQVLIYLGSNRA

SGVPDRFSGSGSGTDFTLKISRVEAEDVGLYYCMQTLQTPWTFGQGTKVEIK

Heavy chain variable region N33F[VH]; P53R[VH]; Q27R[VL]
(SEQ ID NO: 18)
QVQLVQSGAEVKKPGAPVKVSCETSGYRFSDYFVHWVRQAPGQGPEWIGRISRNSGGT

KYAQKFQGRVTMTRDMSMNTAYMELSGLRSDDTAVYYCVRGHCDGTTCSRAYWGQ

GTLVTVSS

Light chain variable region N33F[VH]; P53R[VH]; Q27R[VL]
(SEQ ID NO: 17)
DVVMTQSPLSLPVTPGEPASISCRSSRSLLHRSGHKYLHWYLQRPGQSPQVLIYLGSNRA

SGVPDRFSGSGSGTDFTLKISRVEAEDVGLYYCMQTLQTPWTFGQGTKVEIK

Heavy chain variable region S30R[VH]; N33F[VH]; S52R[VH]
(SEQ ID NO: 19)
QVQLVQSGAEVKKPGAPVKVSCETSGYRFRDYFVHWVRQAPGQGPEWIGRIRPNSGGT

KYAQKFQGRVTMTRDMSMNTAYMELSGLRSDDTAVYYCVRGHCDGTTCSRAYWGQ

GTLVTVS

Light chain variable region S30R[VH]; N33F[VH]; S52R[VH]
(SEQ ID NO: 14)
DVVMTQSPLSLPVTPGEPASISCRSSQSLLHRSGHKYLHWYLQRPGQSPQVLIYLGSNRA

SGVPDRFSGSGSGTDFTLKISRVEAEDVGLYYCMQTLQTPWTFGQGTKVEIK

Heavy chain variable region S30R[VH]; N33F[VH]; P53R[VH]
(SEQ ID NO: 20)
QVQLVQSGAEVKKPGAPVKVSCETSGYRFRDYFVHWVRQAPGQGPEWIGRISRNSGGT

KYAQKFQGRVTMTRDMSMNTAYMELSGLRSDDTAVYYCVRGHCDGTTCSRAYWGQ

GTLVTVSS

Light chain variable region S30R[VH]; N33F[VH]; P53R[VH]
(SEQ ID NO: 14)
DVVMTQSPLSLPVTPGEPASISCRSSQSLLHRSGHKYLHWYLQRPGQSPQVLIYLGSNRA

SGVPDRFSGSGSGTDFTLKISRVEAEDVGLYYCMQTLQTPWTFGQGTKVEIK

Tau protein 2N4R:
(SEQ ID NO: 21)
MAEPRQEFEVMEDHAGTYGLGDRKDQGGYTMHQDQEGDTDAGLKESPLQTPTEDGSE

EPGSETSDAKSTPTAEDVTAPLVDEGAPGKQAAAQPHTEIPEGTTAEEAGIGDTPSLEDE

AAGHVTQARMVSKSKDGTGSDDKKAKGADGKTKIATPRGAAPPGQKGQANATRIPAK

TPPAPKTPPSSGEPPKSGDRSGYSSPGSPGTPGSRSRTPSLPTPPTREPKKVAVVRTPPKSP

SSAKSRLQTAPVPMPDLKNVKSKIGSTENLKHQPGGGKVQIINKKLDLSNVQSKCGSKD

NIKHVPGGGSVQIVYKPVDLSKVTSKCGSLGNIHHKPGGGQVEVKSEKLDFKDRVQSKI

-continued

GSLDNITHVPGGGNKKIETHKLTFRENAKAKTDHGAEIVYKSPVVSGDTSPRHLSNVSST

GSIDMVDSPQLATLADEVSASLAKQGL

Tau peptide V1089-24:

(SEQ ID NO: 9)

412-SSTGSIDMVDpSPQLATLA-429

---

The invention claimed is:

1. A binding molecule that is capable of specifically binding to tau, selected from the group consisting of:

a binding molecule comprising a heavy chain CDR1 comprising the amino acid sequence of SEQ ID NO: 1, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6;

a binding molecule comprising a heavy chain CDR1 comprising the amino acid sequence of SEQ ID NO: 8, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 10, a light chain CDR2 comprising the amino acid sequence of SEQ ID NO: 5, and a light chain CDR3 comprising the amino acid sequence of SEQ ID NO: 6;
a binding molecule comprising a heavy chain CDR1 comprising the amino acid sequence of SEQ ID NO: 8, a heavy chain CDR2 comprising the amino acid sequence of SEQ ID NO: 11, a heavy chain CDR3 comprising the amino acid sequence of SEQ ID NO: 3, a light chain CDR1 comprising the amino acid sequence of SEQ ID NO: 10, a light chain CDR2 comprising the amino acid sequence of SEQ ID NO: 5, and a light chain CDR3 comprising the amino acid sequence of SEQ ID NO: 6;
a binding molecule comprising a heavy chain CDR1 comprising the amino acid sequence of SEQ ID NO: 12, a heavy chain CDR2 comprising the amino acid sequence of SEQ ID NO: 7, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6; and
a binding molecule comprising a heavy chain CDR1 comprising the amino acid sequence of SEQ ID NO: 12, a heavy chain CDR2 comprising the amino acid sequence of SEQ ID NO: 11, a heavy chain CDR3 comprising the amino acid sequence of SEQ ID NO: 3, a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6.

2. The binding molecule according to claim 1, wherein the binding molecule comprises a heavy chain variable region comprising an amino acid sequence selected from the group consisting of SEQ ID NO: 15, 16, 18, 19 and 20, and a light chain variable region selected from the group consisting of SEQ ID NO: 14 and 17.

3. The binding molecule according to claim 2, wherein the binding molecule is selected from the group consisting of:
a binding molecule comprising a heavy chain variable region comprising the amino acid sequence of SEQ ID NO: 15 and a light chain variable region comprising the amino acid sequence of SEQ ID NO: 14;
a binding molecule comprising a heavy chain variable region comprising the amino acid sequence of SEQ ID NO: 16 and a light chain variable region comprising the amino acid sequence of SEQ ID NO: 14;
a binding molecule comprising a heavy chain variable region comprising the amino acid sequence of SEQ ID NO: 16 and a light chain variable region comprising the amino acid sequence of SEQ ID NO: 17;
a binding molecule comprising a heavy chain variable region comprising the amino acid sequence of SEQ ID NO: 18 and a light chain variable region comprising the amino acid sequence of SEQ ID NO: 17;
a binding molecule comprising a heavy chain variable region comprising the amino acid sequence of SEQ ID NO: 19 and a light chain variable region comprising the amino acid sequence of SEQ ID NO: 14; and
a binding molecule comprising a heavy chain variable region comprising the amino acid sequence of SEQ ID NO: 20 and a light chain variable region comprising the amino acid sequence of SEQ ID NO: 14.

4. The binding molecule according to claim 1, wherein the binding molecule is a human IgG1 antibody, or an antigen-binding fragment thereof.

5. A method of inhibiting spreading of tau protein aggregates and/or mediating uptake and degradation of tau aggregates by microglia by administering a binding molecule according to claim 1 to a patient in need thereof.

6. A method of diagnosing and/or ameliorating symptoms of neurodegenerative diseases that involves pathological aggregation of tau by administering a binding molecule according to claim 1 to a patient in need thereof.

7. The method according to claim 6, wherein the neurodegenerative disease is Alzheimer's disease.

8. An immunoconjugate, comprising at least one binding molecule according to claim 1, further comprising at least one tag.

9. A nucleic acid molecule encoding a binding molecule according to claim 1.

10. A vector comprising a nucleic acid molecule according to claim 9.

11. The binding molecule according to claim 3, wherein the binding molecule is a human IgG1 antibody, or an antigen-binding fragment thereof.

12. A method of inhibiting spreading of tau protein aggregates and/or mediating uptake and degradation of tau aggregates by microglia by administering a binding molecule according to claim 3 to a patient in need thereof.

13. A method of diagnosing and/or ameliorating symptoms of neurodegenerative diseases that involves pathological aggregation of tau by administering a binding molecule according to claim 3 to a patient in need thereof.

14. The method according to claim 13, wherein the neurodegenerative disease is Alzheimer's disease.

15. A nucleic acid molecule encoding a binding molecule according to claim 3.

16. A vector comprising a nucleic acid molecule according to claim 15.

17. A pharmaceutical composition comprising:
the binding molecule according to claim 1;
an immunoconjugate, comprising the binding molecule according to claim 1 and at least one tag; or
a combination thereof.

18. The binding molecule according to claim 1, wherein the binding molecule is a human IgG1 antibody.

19. The binding molecule according to claim 3, wherein the binding molecule is a human IgG1 antibody.

* * * * *

SEQUENCE LISTING

<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<223> OTHER INFORMATION: CBTAU 22.1 HCDR1

<400> SEQUENCE: 1

Gly Tyr Arg Phe Ser Asp Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: CBTAU 22.1 HCDR2

<400> SEQUENCE: 2

Ile Ser Pro Asn Ser Gly Gly Thr
1               5

<210> SEQ ID NO 3
<211> LENGTH: 14
<212> TYPE: PRT
<213> ORGANISM: Artificial Sequence
<220> FEATURE:
<223> OTHER INFORMATION: CBTAU HCDR3

<400> SEQUENCE: 3

Val Arg Gly His Cys Asp Gly Thr Thr Cys Ser Arg Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CBTAU 22.1 LCDR1

<400> SEQUENCE: 4

Gln Ser Leu Leu His Arg Ser Gly His Lys Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: CBTAU 22.1 LCDR2

<400> SEQUENCE: 5

Leu Gly Ser
1

```
<210> SEQ ID NO 6
<211> LENGTH: 9
<212> TYPE: PRT
<213> ORGANISM: Artificial Sequence
<220> FEATURE:
<223> OTHER INFORMATION: CBTAU LCDR3

<400> SEQUENCE: 6

Met Gln Thr Leu Gln Thr Pro Trp Thr
1               5

<210> SEQ ID NO 7
<211> LENGTH: 8
<212> TYPE: PRT
<213> ORGANISM: Artificial Sequence
<220> FEATURE:
<223> OTHER INFORMATION: S52A R[VH]_HC  CDR2

<400> SEQUENCE: 7

Ile Arg Pro Asn Ser Gly Gly Thr
1               5

<210> SEQ ID NO 8
<211> LENGTH: 8
<212> TYPE: PRT
<213> ORGANISM: Artificial Sequence
<220> FEATURE:
<223> OTHER INFORMATION: N33F[VH];S52A R[VH]_HC CDR1

<400> SEQUENCE: 8

Gly Tyr Arg Phe Ser Asp Tyr Phe
1               5

<210> SEQ ID NO 9
<211> LENGTH: 19
<212> TYPE: PRT
<213> ORGANISM: Artificial Sequence
<220> FEATURE:
<223> OTHER INFORMATION: Tau peptide V1089-24

<400> SEQUENCE: 9

Ser Ser Thr Gly Ser Ile Asp Met Val Asp Pro Ser Pro Gln Leu Ala
1               5                   10                  15

Thr Leu Ala

<210> SEQ ID NO 10
<211> LENGTH: 11
<212> TYPE: PRT
<213> ORGANISM: Artificial Sequence
<220> FEATURE:
<223> OTHER INFORMATION: N33F[VH];S52A R[VH];Q27R [VL]_LC  CDR1

<400> SEQUENCE: 10

Arg Ser Leu Leu His Arg Ser Gly His Lys Tyr
1               5                   10

<210> SEQ ID NO 11
<211> LENGTH: 8
<212> TYPE: PRT
<213> ORGANISM: Artificial Sequence
<220> FEATURE:
<223> OTHER INFORMATION: N33F[VH];P52AR[VH];Q27R [VL]_HC CDR2

<400> SEQUENCE: 11

Ile Ser Arg Asn Ser Gly Gly Thr
1               5
```

<210> SEQ ID NO 12
<211> LENGTH: 8
<212> TYPE: PRT
<213> ORGANISM: Artificial Sequence
<220> FEATURE:
<223> OTHER INFORMATION: S30R[VH];N33F[VH];S52A R [VH]_HC CDR1

<400> SEQUENCE: 12

Gly Tyr Arg Phe Arg Asp Tyr Phe
1               5

<210> SEQ ID NO 13
<211> LENGTH: 121
<212> TYPE: PRT
<213> ORGANISM: Artificial Sequence
<220> FEATURE:
<223> OTHER INFORMATION: Heavy chain variable region CBTAU-22.1

<400> SEQUENCE: 13

Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Ser Asp Tyr
            20                  25                  30

Asn Val His Trp Val Arg Gln Ala Pro Gly Gln Gly Pro Glu Trp Ile
        35                  40                  45

Gly Arg Ile Ser Pro Asn Ser Gly Gly Thr Lys Tyr Ala Gln Lys Phe
    50                  55                  60

Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr Trp Gly
            100                 105                 110

Gln Gly Thr Leu Val Thr Val Ser Ser
        115                 120

<210> SEQ ID NO 14
<211> LENGTH: 112
<212> TYPE: PRT
<213> ORGANISM: Artificial Sequence
<220> FEATURE:
<223> OTHER INFORMATION: Light chain variable region CBTAU-22.1

<400> SEQUENCE: 14

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Ser Gly His Lys Tyr Leu His Trp Tyr Leu Gln Arg Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Thr
                85                  90                  95

Leu Gln Thr Pro Trp Thr Phe Gly Gln Gly Thr Lys Val Glu Ile Lys
            100                 105                 110

<210> SEQ ID NO 15
<211> LENGTH: 121
<212> TYPE: PRT
<213> ORGANISM: Artificial Sequence
<220> FEATURE:
<223> OTHER INFORMATION: Heavy chain variable region [S52R]

<400> SEQUENCE: 15

```
Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Ser Asp Tyr
            20                  25                  30

Asn Val His Trp Val Arg Gln Ala Pro Gly Gln Gly Pro Glu Trp Ile
        35                  40                  45

Gly Arg Ile Arg Pro Asn Ser Gly Gly Thr Lys Tyr Ala Gln Lys Phe
    50                  55                  60

Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr Trp Gly
            100                 105                 110

Gln Gly Thr Leu Val Thr Val Ser Ser
        115                 120
```

<210> SEQ ID NO 16
<211> LENGTH: 121
<212> TYPE: PRT
<213> ORGANISM: Artificial Sequence
<220> FEATURE:
<223> OTHER INFORMATION: Heavy chain variable region N33F[VH];S52R[VH]

<400> SEQUENCE: 16

```
Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Ser Asp Tyr
            20                  25                  30

Phe Val His Trp Val Arg Gln Ala Pro Gly Gln Gly Pro Glu Trp Ile
        35                  40                  45

Gly Arg Ile Arg Pro Asn Ser Gly Gly Thr Lys Tyr Ala Gln Lys Phe
    50                  55                  60

Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr Trp Gly
            100                 105                 110

Gln Gly Thr Leu Val Thr Val Ser Ser
        115                 120
```

<210> SEQ ID NO 17
<211> LENGTH: 112
<212> TYPE: PRT
<213> ORGANISM: Artificial Sequence
<220> FEATURE:
<223> OTHER INFORMATION: Light chain variable region N33F[VH];S52R[VH];
      Q27R[VL]

<400> SEQUENCE: 17

```
Asp Val Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu His Arg
            20                  25                  30

Ser Gly His Lys Tyr Leu His Trp Tyr Leu Gln Arg Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Thr
                85                  90                  95

Leu Gln Thr Pro Trp Thr Phe Gly Gln Gly Thr Lys Val Glu Ile Lys
            100                 105                 110
```

<210> SEQ ID NO 18
<211> LENGTH: 121
<212> TYPE: PRT
<213> ORGANISM: Artificial Sequence
<220> FEATURE:
<223> OTHER INFORMATION: Heavy chain variable region N33F[VH];P53R[VH];
      Q27R[VL]

<400> SEQUENCE: 18

```
Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Ser Asp Tyr
            20                  25                  30

Phe Val His Trp Val Arg Gln Ala Pro Gly Gln Gly Pro Glu Trp Ile
        35                  40                  45

Gly Arg Ile Ser Arg Asn Ser Gly Gly Thr Lys Tyr Ala Gln Lys Phe
    50                  55                  60

Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr Trp Gly
            100                 105                 110

Gln Gly Thr Leu Val Thr Val Ser Ser
        115                 120
```

<210> SEQ ID NO 19
<211> LENGTH: 120
<212> TYPE: PRT
<213> ORGANISM: Artificial Sequence
<220> FEATURE:
<223> OTHER INFORMATION: Heavy chain variable region S30R[VH];N33F[VH];
      S52R[VH]

<400> SEQUENCE: 19

```
Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Arg Asp Tyr
            20                  25                  30

Phe Val His Trp Val Arg Gln Ala Pro Gly Gln Gly Pro Glu Trp Ile
        35                  40                  45

Gly Arg Ile Arg Pro Asn Ser Gly Gly Thr Lys Tyr Ala Gln Lys Phe
    50                  55                  60
```

```
Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr Trp Gly
            100                 105                 110

Gln Gly Thr Leu Val Thr Val Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: Heavy chain variable region S30R[VH];N33F[VH];
      P53R[VH]

<400> SEQUENCE: 20

Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Arg Asp Tyr
                20                  25                  30

Phe Val His Trp Val Arg Gln Ala Pro Gly Gln Gly Pro Glu Trp Ile
            35                  40                  45

Gly Arg Ile Ser Arg Asn Ser Gly Gly Thr Lys Tyr Ala Gln Lys Phe
    50                  55                  60

Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr Trp Gly
            100                 105                 110

Gln Gly Thr Leu Val Thr Val Ser Ser
        115                 120

<210> SEQ ID NO 21
<211> LENGTH: 441
<212> TYPE: PRT
<213> ORGANISM: Artificial Sequence
<220> FEATURE:
<223> OTHER INFORMATION: Tau protein 2N4R

<400> SEQUENCE: 21

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
```

-continued

```
            115                 120                 125
Ser Lys Ser Lys Asp Gly Thr Gly Ser Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440
```